United States Patent [19]
Menyhay

[11] Patent Number: 6,045,539
[45] Date of Patent: *Apr. 4, 2000

[54] STERILE MEDICAL INJECTION PORT AND COVER APPARATUS

[76] Inventor: Steve Z. Menyhay, 9850 N. Willow Creek La., Fresno, Calif. 93720

[*] Notice: This patent is subject to a terminal disclaimer.

[21] Appl. No.: 09/130,841

[22] Filed: Aug. 7, 1998

Related U.S. Application Data

[63] Continuation of application No. 08/708,934, Sep. 6, 1996, Pat. No. 5,792,120, which is a continuation of application No. 08/390,651, Feb. 17, 1995, Pat. No. 5,554,135.

[51] Int. Cl.[7] .................................................. A61M 5/00
[52] U.S. Cl. .................. 604/256; 604/523; 138/89.96 R; 215/DIG. 3
[58] Field of Search .............................. 604/27–29, 93, 604/192, 263, 256, 265, 266, 523, 533, 905; 138/89.96 R; 206/206, 207, 363; 215/DIG. 3

[56] References Cited

U.S. PATENT DOCUMENTS

| D. 342,134 | 12/1993 | Mongeon . | |
|---|---|---|---|
| 4,335,756 | 6/1982 | Sharp . | |
| 4,440,207 | 4/1984 | Genatempo et al. . | |
| 4,573,983 | 3/1986 | Annis | 604/322 |
| 5,267,974 | 12/1993 | Lambert | 604/195 |
| 5,311,985 | 5/1994 | Suida | 206/210 |

OTHER PUBLICATIONS

Keegan–Wells, Diane, R.N., M.S.N., et all *The Use of Venous Access Devices in Pediatric Oncology Nursing Practice.* Journal of Pediatric Oncology Nursing, vol. 9, No. 4, pp. 159–169 (Oct., 1992).

Long, Charlene M., PhD., R.N., et al. *Comparative study of nursing protocols for venous access ports.* Cancer Nursing, vol. 15, No. 1, pp. 18–21 (1992).

Poisson, D.M., et al. *Electron–microscopic description of accretions occurring on tips of infected and non–infected central venous catheters.* Intensive Care Med, vol. 18, pp. 464–468 (1992).

(List continued on next page.)

*Primary Examiner*—Corrine McDermott
*Attorney, Agent, or Firm*—Mark D. Miller

[57] ABSTRACT

A unique external injection port cover is provided that is open at one end, closed at the other end, and includes a set of spiraling screw threads on the inside. It is designed to be screwed into place over a specially adapted external injection port having its own corresponding screw threads. The inside of the closed end of the cover includes an inwardly pointing projection. A sponge is provided inside the open end, and a shatterable plastic capsule containing a combination of antiseptic, bactericidal and virucidal agents is provided between the sponge and the projection. A flexible o-ring seal is provided on the inside of the cover near the open end.

When the present invention is screwed into place over an injection port, the o-ring first creates a seal over the end of the port. As the invention is tightened down, the pressure between the projection and the breakable capsule causes the capsule to rupture thereby releasing the antiseptic agents inside to be soaked up by the sponge. When completely tightened, the antiseptically treated sponge comes into contact with the latex membrane of the port, keeping it saturated, clean and aseptic until the cover is removed. The present injection port cover requires no maintenance when not in use resulting in decreased risk of infection and longer life of the injection port itself.

12 Claims, 7 Drawing Sheets

OTHER PUBLICATIONS

Groeger, Jeffrey S., M.D., et al. *Infectious Morbidity Associated with Long–Term Use of Venous Access Devices in Patients with Cancer.* Annals of Internal Medicine vol. 119, No. 12, pp. 1168–1174 (Dec. 15, 1993).

Larson, Elaine, Ph.D., R.N., F.A.A.N., *APIC Guidelines for Infection Control Practice, Guideline for use of topical antimicrobial agents.* American Journal of Infection Control, vol. 16, No. 6, pp. 253–266, (Dec., 1988).

Marcoux, Charlotte, et al., *Central Venous Access Devices in Children.* Pediatric Nursing, vol. 16, No. 2, pp. 123–133, (Mar.–Apr., 1990).

Forse, R. A., M.D., et al. *Staphylococcus epidermidis: An important pathogen.* Surgery, vol. 86, No. 3, pp. 507–514 (Sep., 1979).

Sitges–Serra, A., M.D., et al. *Catheter sepsis: The clue is the hub.* Surgery, vol. 97, No. 3, pp. 355–357 (Mar., 1985).

STERILE MEDICAL INJECTION PORT AND COVER APPARATUS

This application is a continuation of application Ser. No. 08/708,934 filed Sep. 6, 1996 now U.S. Pat. No. 5,792,120, which is a continuation of application Ser. No. 08/390,651 filed Feb. 17, 1995 now U.S. Pat. No. 5,554,135.

BACKGROUND OF THE INVENTION

The present invention relates to sterile medical injection ports, and more particularly to a new, easy-to-use sterile medical injection port and covering apparatus for hospital and home use.

1. Field of the Invention.

There are many hospital and home care situations where prolonged and frequent access to venous circulation is often necessary for proper patient treatment. Treatments for chronic illnesses, cancer, bacterial infections, AIDS, or those in need of parenteral nutrition or blood transfusions often require repeated daily or even hourly venous punctures. In order to avoid continuous skin punctures in these and other situations, medical Venous Access Devices (VADs) and injection ports have been developed. VADs are also known by such names as atrial catheters, central lines, and central venous catheters.

Presently, there are two basic types of VADs, (a) Partially Implanted Devices (PIDs), and (b) Totally Implanted Devices (TIDs). PIDs may be for short term use where one end of the catheter is inserted into a blood vessel and the other end (where the injection port is located) protrudes from the skin. PIDs may also be for long term use where a catheter is surgically implanted under the skin (under anesthesia), usually in the upper abdomen or chest area, to a vein insertion site. Short term PIDs have been used as long as six months; whereas, long term PIDs have been maintained for more than 2 years.

Totally Implanted Devices (TIDs) such as the Mediport® generally consist of one end of the catheter inserted into a deep venous blood vessel. Placement is similar to a long term PID. However, the access end of a TID is generally in the form of an internal injection port below the surface of the skin.

External injection ports are most commonly used in PIDs. Existing external port devices (i.e. outside of the skin) include a covering membrane or septum which is made of thick silicone or latex. Special needles are required to access the injection port. Such needles have a sharply beveled tip which slices the septum when inserted. When the needle is removed, the septum then reseals. External injection ports must be periodically replaced after repeated punctures.

2. Description of the Prior Art.

The Broviac® catheter (a PID) is a long term small diameter flexible catheter. The Broviac® includes a length of small diameter tubing one end of which is threaded to a desired site inside the body, the other end of which (the access end) dangles from an external opening in the skin. It lies relatively flat against the body after the dressing is in place, and can easily be coiled and secured with tape. The Hickman® catheter (also a PID) has a larger diameter and is used when large volumes of blood, medications, and/or chemotherapy are administered. Single, double and triple access catheters of various sizes are in use in the art.

Surprisingly, no existing injection port is designed for use with a covering for protecting the access port while it is not in use. Some ports include screw threads which allow them to more easily be connected to IV tubing during lengthy accesses. However, most external injection ports normally remain uncovered and completely exposed to the outside world so that the sealed septum membrane is the only barrier to potential contaminants. These contaminants include, but are not limited to, germs, bacteria, air, dirt, clothing, skin and perspiration. Injection ports (especially those attached to the dangling Broviac® catheter) are also exposed to potential trauma and rough handling. Children and other unknowing patients may subject the port to damage from the insertion of dirty sharp objects or playthings, chewing on the port, etc. Also, exposure of the latex port septum to agents such as ozone, oxygen, and ultra violet light can cause the latex to break down over time.

Because of the exposure of the injection port to contaminants, the use of an aseptic cleansing procedure is required prior to accessing the port for administration of medication. Using currently accepted techniques, the cleansing process alone involves several steps and the use of numerous materials for each port access. In order to assure an aseptic environment, a second person is needed to assist the first with the cleansing process. This is because the iodine and alcohol swabs are sealed inside sterile pouches, the outsides of which are not sterile. Hence, touching the outside with a sterile glove contaminates the glove. The second person opens the pouches allowing the first to remove the contents. Otherwise, the first person contaminates his/her gloves by opening the pouches.

A typical example of an external injection port access and cleansing procedure includes the following time consuming steps:

| Steps | Equipment |
| --- | --- |
| 1. Wash hands | |
| 2. Put on sterile gloves (RN only) | 1 pair of qloves |
| 3. Assistant opens first alcohol swab package | |
| 4. RN wipes injection port with alcohol | 1 alcohol swab |
| 5. Assistant opens first povidone iodine swab | 1 povidone iodine swab |
| 6. RN takes swab and wipes injection port with it | |
| 7. Assistant opens second povidone iodine swab | 1 povidone iodine swab |
| 8. RN takes swab and wipes injection port with it | |
| 9. Assistant opens third povidone iodine swab | 1 povidone iodine swab |
| 10. Wait 30 seconds after third iodine wipe | |
| 11. Assistant opens first alcohol swab | 1 alcohol swab |
| 12. RN takes swab and wipes injection port with it | |
| 13. Assistant opens second alcohol swab | 1 alcohol swab |
| 14. RN takes swab and wipes injection port with it | |
| 15. Assistant opens third alcohol swab | 1 alcohol swab |
| 16. RN takes swab and wipes injection port with it | |
| 17. Access port; administer medication | |
| 18. Leave injection port dangling and exposed | |

Then, as soon as the port is released, it will come into contact with the patient's skin or clothing and immediately become dirty again, making the above procedure necessary the next time the port is accessed. These cumbersome techniques and materials are required because of the poor design of the current art. In a hospital or clinic setting, trained nurses generally perform the procedure. However, despite having the best of intentions and necessary training, the pressures of the moment, combined with occasional unavailability of the required medical supplies or personnel (e.g. only 1 alcohol swab instead of 3, no assistant available, etc.) can result in missed steps or failure to follow proper procedures.

The cleansing procedure, if properly followed, is very time consuming. Materials must be gathered prior to access, and an assistant must be available before the procedure can be started. Then, the procedure itself, as outlined above, requires careful and strict performance of a long series of time consuming aseptic steps, and results in a messy accumulation of used swabs and stains when the procedure is completed.

In a home setting, rigorous and extensive training of the involved family members is required. They must understand the principles of aseptic technique and catheter safety, as well as the specific tasks of dressing changes, changing injection ports, and emergency measures. Even with such training, these steps can seem complicated to the ordinary user resulting in missed or poorly performed steps which can compromise asepsis, thereby increasing the risk of infection. The more frequent the access, the greater the risk. Often, home care providers will erroneously conclude that if the injection port was cleaned once early in the day, it need not be cleaned again that day, or a lesser cleansing procedure is required for subsequent accesses that day. In other situations, the very condition for which the patient is being treated (e.g. AIDS, cancer, etc.) places them at greater risk of infection and death, making the need for asepsis of paramount importance.

An average cost to a hospital for a pair of sterile gloves is in the range of three dollars. An average home care cost for sterile gloves is usually higher, in the range of five dollars per pair. An average hospital cost for a box of isopropyl alcohol wipes is in the range of two dollars. An average home care cost for the same box again is higher, usually in the range of twelve dollars. An average hospital cost for a box of povidone iodine pads is in the range of three dollars. An average home care cost for the same box is higher, usually in the range of twenty dollars.

Thus, an average hospital cost (materials only, not labor) of sterile supplies for each injection port access may be in the range of seven dollars ($7.00) per access. Multiple daily accesses compound and increase these costs even more. Every external injection port must be accessed at least once a day for the application of heparin to prevent clotting. The costs of such materials for home care services are generally much higher, as set forth above, and can easily be double or triple the hospital costs. Thus, on a typical multiple access day, a home care provider may spend well over thirty dollars ($30.00) simply for materials to clean and access the dirty dangling injection port.

Recent scientific studies have concluded that the external injection port, sometimes called the catheter hub, is the place of origin of bacteria infecting catheter tips. These studies recommend that manipulation of the hub be kept at a minimum, and that a more rigorous approach to aseptic technique be undertaken. However, as described above, these are time consuming, expensive and difficult measures. One study suggests that the hub be properly covered. However, this study fails to propose any cover design, and instead simply indicates that new designs are needed to assure better protection against environmental soiling.

All external injection ports should have protective coverings in order to maintain the aseptic integrity of the port and medical tubing, and to reduce the risk of infection or other complications stemming from unwanted external environmental factors. However, despite this great need, no suitable cover has ever been developed.

SUMMARY OF THE INVENTION

The present invention overcomes many of the drawbacks and avoids much of the cost associated with cleaning present external injection port devices by providing a unique external injection port cover. The cover is open at one end, closed at the opposite end, and includes spiraling screw threads on the inside. The inside of the closed end includes an inwardly pointing projection. A shatterable plastic capsule containing a combination of antiseptic, bactericidal and virucidal agents is provided inside the cover immediately adjacent to the projection. A sponge is provided inside the cover next to the capsule on the side opposite from the projection. A flexible annular ring (o-ring) is provided on the inside of the cover near the open end. The cover is designed to be screwed into place over a specially adapted external injection port having its own corresponding screw threads.

As the screw threads of the present invention are tightened over the injection port, the o-ring first creates a seal over the end of the port. Then, as the tightening continues, the pressure between the inwardly pointing projection and the capsule causes the capsule to break, releasing the antiseptic agents to be soaked up by the sponge. When the tightening is complete, the antiseptically treated sponge is in contact with the latex membrane of the port, keeping it bathed and in a clean and aseptic condition until the cover is removed.

Upon removal, since the surface of the port is already in an aseptic condition, there is no need to follow lengthy cleansing procedures or utilize expensive cleansing materials to access the injection port. Thus, the need for sterile gloves, alcohol swabs, iodine swabs, and/or an assistant are eliminated. After access, the used cover is discarded and a new one is taken from a sealed sterilized package and screwed into place over the injection port to again assure that the port remains in a clean and aseptic condition.

These simple and straight forward steps can be easily followed by a nurse, home care provider, or family member with little chance for mistakes, thereby assuring a safer and cleaner environment for the injection port.

It is therefore a primary object of the present invention to provide a unique protective covering for use on an external injection port that will help keep the surface of the port in a aseptic condition while covered.

It is a further important object of the present invention to provide a protective covering for an external injection port that will help prevent contamination of the port from the outside.

It is a further important object of the present invention to provide a protective covering for an external injection port that eliminates the need for following strict and complicated cleansing procedures every time the port is accessed.

It is a further important object of the present invention to provide a protective covering for an external injection port that eliminates the need for using sterile gloves, iodine swabs, and alcohol swabs every time the port is accessed.

It is a further important object of the present invention to provide a protective covering for an external injection port that eliminates the mess created by using sterile gloves, iodine swabs, and alcohol swabs every time the port is accessed.

It is a further object of the present invention to provide a protective covering for an external injection port that is simple, fast, and easy-to-use, especially in home care situations.

It is a further object of the present invention to provide a protective covering for an external injection port that helps protect the port from puncture or trauma from outside objects or forces.

It is a further object of the present invention to provide a protective covering for an external injection port that promotes a clean injection port environment and provides an extra barrier to contamination of the port by germs, bacteria, and the like.

It is a further object of the present invention to provide a protective covering for an external injection port that provides a continuous aseptic immersion (bathing) of the injection port.

It is a further object of the present invention to provide a protective covering for an external injection port that helps reduce the risk of infection of the patient using the port.

It is a further object of the present invention to provide a fast, easy and low maintenance method of accessing an injection port in a aseptic manner.

It is a further object of the present invention to provide a simple and low cost method and apparatus for protectively covering an external injection port.

It is a further important object of the present invention to provide the combination of an injection port and cover device that will help keep the surface of the port in an aseptic condition while covered.

It is a further important object of the present invention to provide the combination of an injection port and cover device that will help prevent contamination of the port from the outside.

It is a further important object of the present invention to provide the combination of an injection port and cover device that eliminates the need for following strict and complicated cleansing procedures every time the port is accessed.

It is a further important object of the present invention to provide the combination of an injection port and cover device that eliminates the need for using sterile gloves, iodine swabs, and alcohol swabs every time the port is accessed.

It is a further important object of the present invention to provide the combination of an injection port and cover device that eliminates the mess created by using sterile gloves, iodine swabs, and alcohol swabs every time the port is accessed.

It is a further object of the present invention to provide the combination of an injection port and cover device that is simple, fast, and easy-to-use, especially in home care situations.

It is a further object of the present invention to provide the combination of an injection port and cover device that helps protect the port from puncture or trauma from outside objects or forces.

It is a further object of the present invention to provide the combination of an injection port and cover device that promotes a clean injection port environment and provides an extra barrier to contamination of the port by germs, bacteria, and the like.

It is a further object of the present invention to provide the combination of an injection port and cover device that provides a continuous aseptic immersion (bathing) of the injection port.

It is a further object of the present invention to provide the combination of an injection port and cover device that helps reduce the risk of infection of the patient using the port.

Additional objects of the invention will be apparent from the detailed descriptions and the claims herein.

DETAILED DESCRIPTION OF THE DRAWINGS

Figure 1:
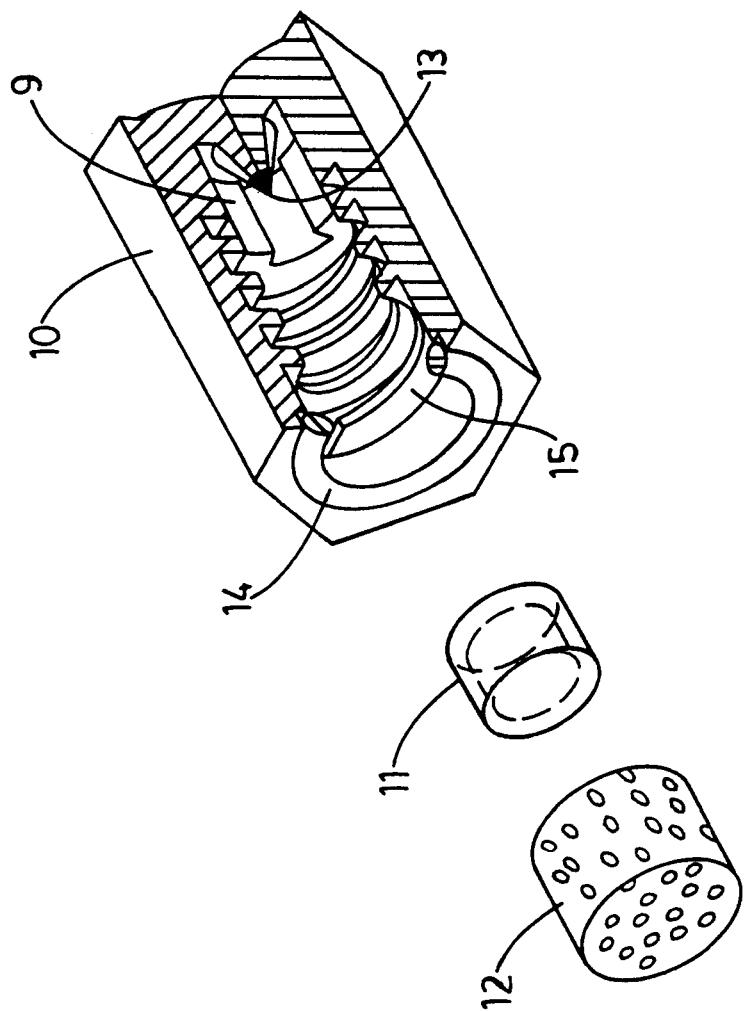
FIG. 1 is an exploded partially cut away perspective view of the external injection port covering of the present invention.
Figure 2:
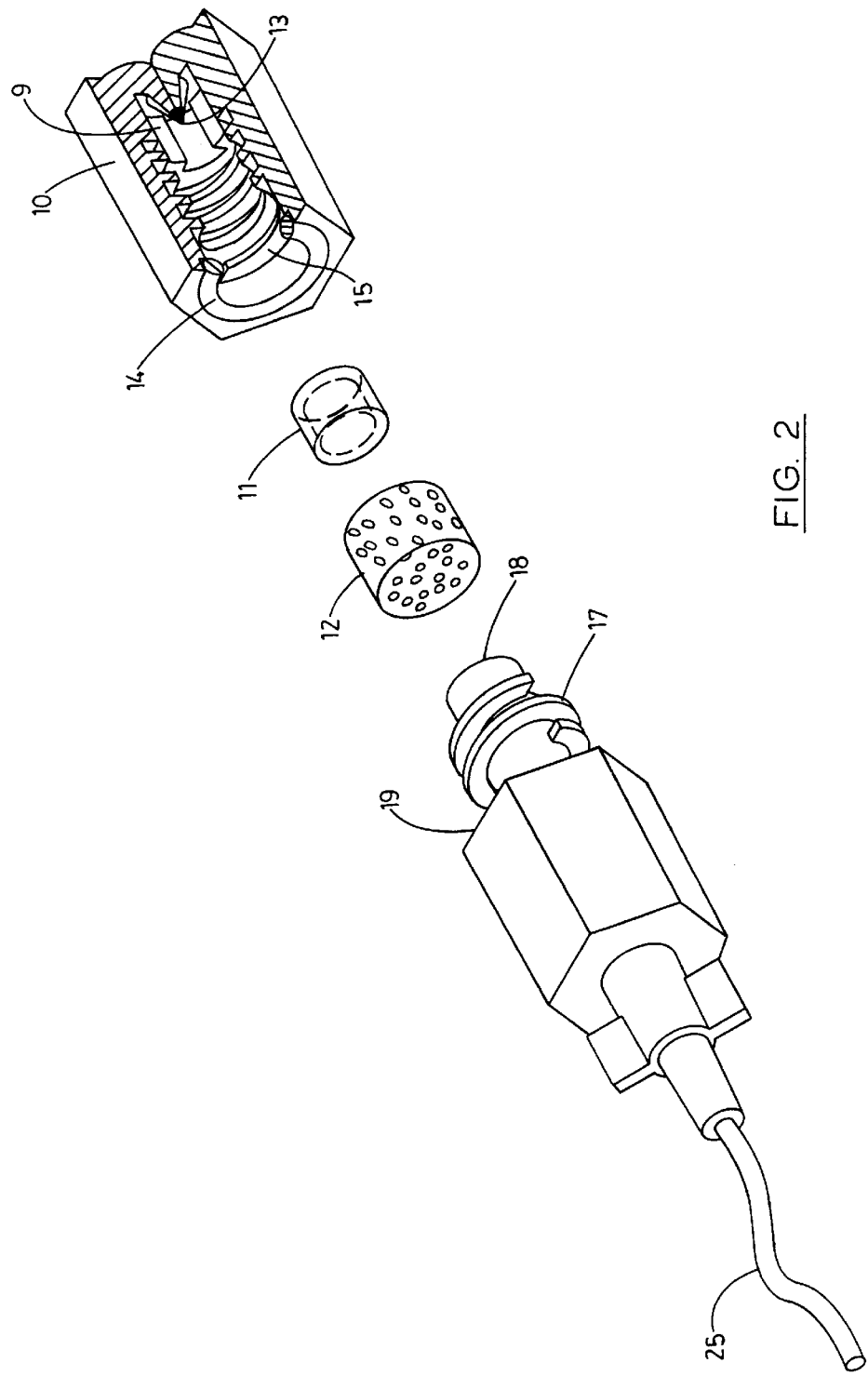
FIG. 2 is an exploded partially cut away perspective and diagrammatic view of an external injection port catheter, and the covering of the present invention.

Referring to the drawings wherein like reference characters designate like or corresponding parts throughout the several views, and referring particularly to FIGS. 1 and 2, it is seen that the invention includes a cylinder 10 that is open on one end, having a set of screw threads 15 on the inside thereof. An inwardly pointing projection 13 is provided on the inside of cylinder 10 at the closed end. A rubberized annular o-ring 14 is provided at or near the open end of cylinder 10.

Figure 5:
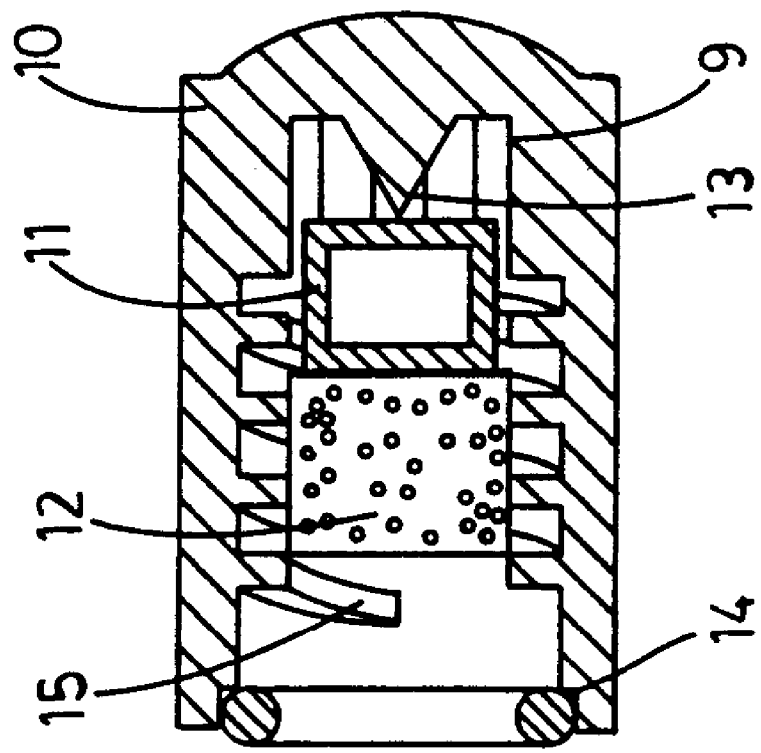
FIG. 5 is a side cutaway view of the external injection port cover of the present invention with the capsule and sponge inside.
Figure 6:
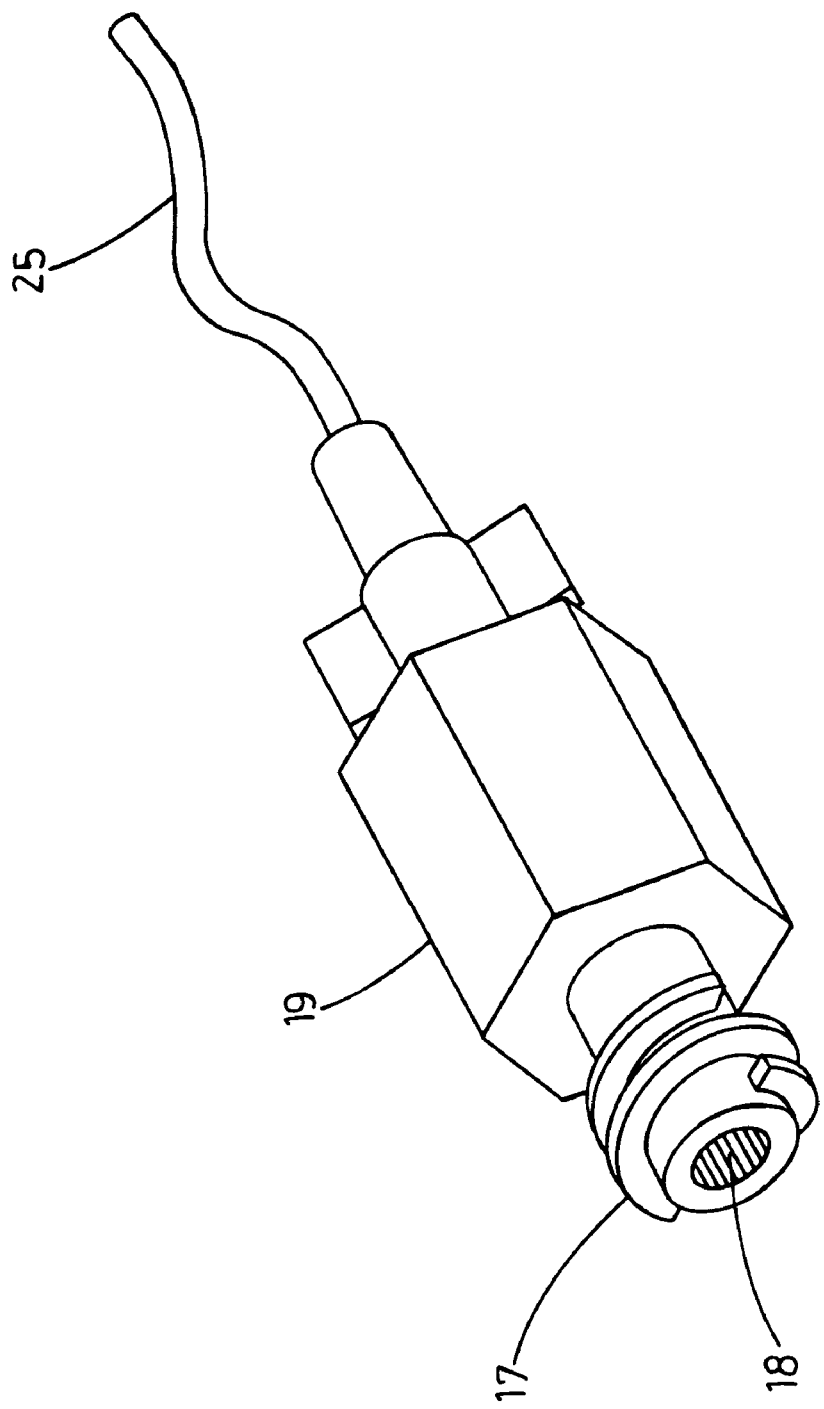
FIG. 6 is a perspective view of a specially adapted port having hexagonal sides for use with the cover of the present invention.

A breakable capsule 11 is disposed inside cylinder 10 immediately adjacent to projection 13 (see FIG. 5). A small sponge 12 is provided inside cylinder 10 next to capsule 11 on the side opposite projection 13. Capsule 11 is filled with a solution containing povidone iodine and isopropyl alcohol (an antiseptic, bactericidal and virucidal solution). Capsule 11 is made of a breakable plastic material so that it will rupture when it is pressed firmly against projection 13.

External injection port 19 includes a thick septum 18 made of resealable latex material. A set of screw threads 17 are provided on port 19 which match up with screw threads 15 on cover 10 so that port 19 may be easily screwed into cover 10 (much like a bolt into a nut). Catheter 25 is attached to the port and leads back to the body of the patient.

Figure 3:
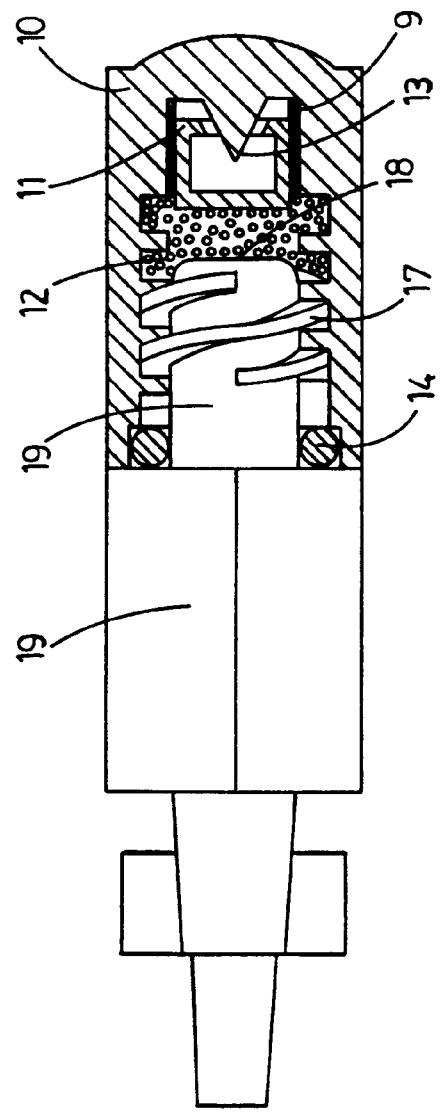
FIG. 3 is a partially cut away side view showing the cover and port of the present invention after the cover has been tightly screwed over the port and the antiseptic capsule ruptured.
Figure 4:
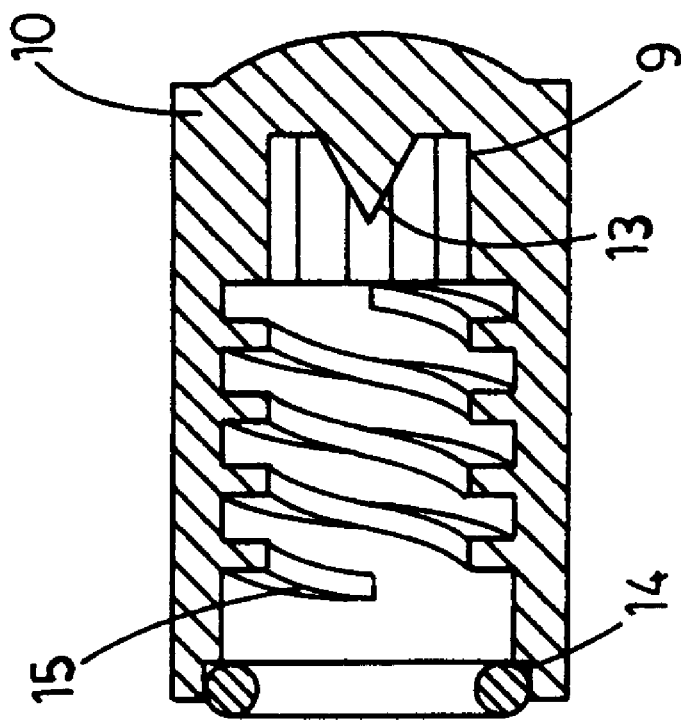
FIG. 4 is a side cutaway view of the external injection port cover of the present invention without the capsule or sponge inside.

When the present invention is screwed into place over the injection port, o-ring 14 first creates a seal over the end of the port 19 (see FIG. 3). As the invention is tightened, the pressure between projection 13 and breakable capsule 11 causes the capsule to rupture thereby releasing the antiseptic agents inside to be soaked up by sponge 12. Grooves 9 on the inside of cylinder 10 act as channels that allow the antiseptic agents escaping from ruptured capsule 11 to flow around the capsule and soak into sponge 12. When completely tightened, the antiseptically treated sponge 12 comes into contact with the latex membrane 18 of the port, aseptically bathing the port until the cover is removed.

The present invention can be used not only to cover but also to aseptically cleanse the surface of an injection port simply by being firmly attached thereto. The cover of the present invention should be placed on the injection port during the surgical placement of the catheter, and replaced every time the port is either accessed or replaced. The following illustrates a typical procedure using the present invention:

1. Wash hands.
2. Open sterile envelope containing new sterile replacement cover, leaving cover inside but easily accessible.
3. Unscrew old cover from port and discard.
4. Access port; administer medication.
5. Remove new cover from envelope and screw firmly into place over port.

Note that the extra person and the extra steps of applying sterile gloves, using iodine swabs, and using alcohol swabs are not needed. There is none of the mess associated with iodine stains, or the disposal of many wrappers and swabs. The procedure is extremely simple, straight forward and easy-to-follow, thereby promoting fewer mistakes and reducing the risk of infection.

Figure 7:
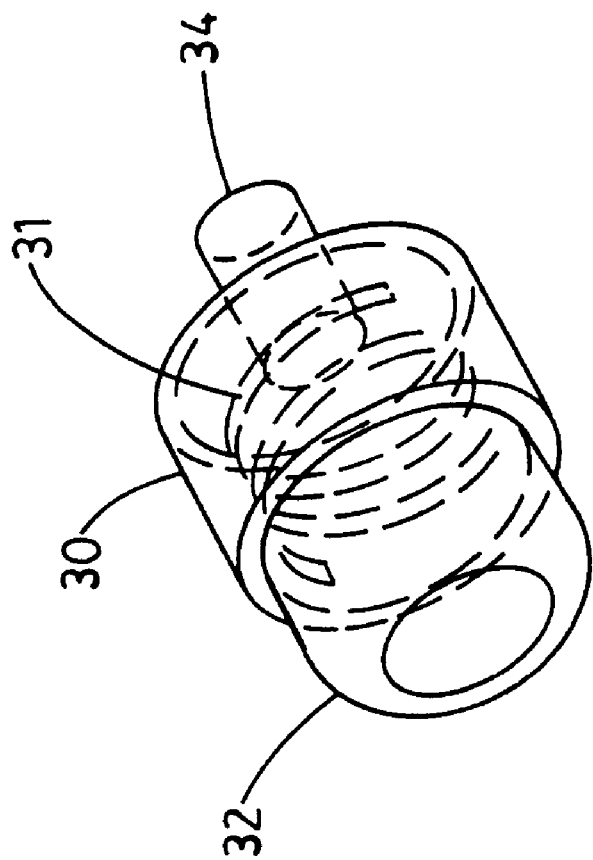
FIG. 7 is a perspective view of a prior art injection port.

A prior art port and hub is shown in FIG. 7. This hub includes an access port 32, a hub housing 30 and a set of internal screw threads 31 which allow the hub to be attached to the female end of a luer lock of an existing Broviac® or Hickman® catheter. Tube 34 attaches the hub to such a catheter 25.

DESCRIPTION OF THE PREFERRED EMBODIMENTS

In the preferred embodiment, the cylindrical cover cap of the present invention is made of lightweight rigid non-porous plastic such as polynylon. The outer edges of the cylinder may be smooth, hexagonal, octagonal, ridged, etc. The cylinder may be of various sizes and lengths depending upon the port to which it is to be attached. The annular o-ring should be made of a durable, sealable, flexible rubberized material such as fluorosilicone. The projection inside the cover should be large enough and sufficiently pointed to cause the capsule to break when the capsule is pressed against it. The capsule itself should be small enough to fit snugly inside the cover, and be made of a thin-layered brittle plastic (such as acrylic) that can be sealed in order to hold the fluid of the antiseptic, but which will rupture under nominal pressure. It should not be made of glass. The sponge should be small enough to fit inside the cover, and should have an absorption capacity roughly equal to or slightly less than the volume of fluid contained in the capsule. The sponge should be porous, but firm enough to transmit pressure to the capsule.

The helical screw threads can be of any size that is small enough to allow at least two complete circuits, thereby assuring a tight seal. The outside of the cover should be easily gripped, and is hexagonal in the preferred embodiment; however, it could also be rectangular, octagonal, rounded with ridges, etc. The outside of the corresponding port should be the same as the cover so that the two screw together into a single lightweight unit. The circumference of the inside of the cover should be slightly larger than the circumference of the stem of the port; and the circumference of the inside of the o-ring should be slightly narrower than the circumference of the stem of the port in order to effect a good seal. The septum of the port should be made of a thick latex material.

It is to be understood that variations and modifications of the present invention may be made without departing from the scope thereof. It is also to be understood that the present invention is not to be limited by the specific embodiments disclosed herein, but only in accordance with the appended claims when read in light of the foregoing specification.

I claim:

1. A protective cover for an external injection port comprising:
   a. a hollow cylindrical housing having an opening in the form of a bore on one end thereof said opening having a set of helical screw threads on the inside thereof, a closed opposite end, a projection on the inside of said closed end, and an annular rubberized seal on the inside of said bore at the open end;
   b. a pad of absorbent porous material disposed inside said bore; and
   c. a frangible sealed capsule disposed inside said bore between said projection and said pad, said capsule containing antiseptic material.

2. A cover for an external injection port comprising a protective cap having an opening therein said opening being specially adapted to receive an external injection port, said opening also holding a frangible capsule containing a reservoir of antiseptic material.

3. The cover described in claim 2 wherein said capsule ruptures upon coupling the cover to the port in order to release the antiseptic material contained therein.

4. The cover described in claim 3 wherein an absorbent pad is provided in said opening adjacent to said capsule such that upon the rupture of said capsule, said pad is soaked with antiseptic material.

5. The cover described in claim 4 wherein said pad is deployed in said cover so that it comes into contact with said port upon coupling of the cover to the port.

6. The cover described in claim 3 wherein a projection is provided inside said cover to facilitate rupturing said capsule when said cover is tightened over said port.

7. The cover described in claim 3 wherein the antiseptic material contained in said capsule is comprised of at least one material selected from the group including povidone iodine and isopropyl alcohol.

8. The cover described in claim 2 wherein an absorbent pad is provided in said opening adjacent to said reservoir.

9. The cover described in claim 2 where in said cap is cylindrical in shape and has a closed end.

10. The cover described in claim 2 wherein helical threads are provided inside said opening and corresponding helical threads are provided on said port for engagement of said cover to said port.

11. The cover described in claim 2 wherein an annular rubberized seal is provided inside said cover for airtight attachment creating a closed aseptic environment over said port.

12. The combination of an external injection port and cover therefor, comprising an external injection port having a septum at one end thereof and a removable protective cap having an opening therein for covering said septum, said opening also containing a frangible capsule containing a reservoir of antiseptic material.

* * * * *